(12) United States Patent
Pfeiffer et al.

(10) Patent No.: US 7,314,449 B2
(45) Date of Patent: Jan. 1, 2008

(54) APPARATUS FOR DETERMINING CARDIOVASCULAR PARAMETERS

(75) Inventors: Ulrich J. Pfeiffer, München (DE); Thorsten Burger, München (DE)

(73) Assignee: Pulsion Medical Systems AG, Munich (DE)

( * ) Notice: Subject to any disclaimer, the term of this patent is extended or adjusted under 35 U.S.C. 154(b) by 523 days.

(21) Appl. No.: 10/743,515

(22) Filed: Dec. 22, 2003

(65) Prior Publication Data

US 2004/0249297 A1    Dec. 9, 2004

(30) Foreign Application Priority Data

Dec. 23, 2002    (DE) ................ 102 60 762

(51) Int. Cl.
*A61B 5/02*    (2006.01)
(52) U.S. Cl. .................... 600/481; 600/485; 600/508
(58) Field of Classification Search ............... 600/481, 600/508
See application file for complete search history.

(56) References Cited

U.S. PATENT DOCUMENTS

| | | | | |
|---|---|---|---|---|
| 5,316,004 | A * | 5/1994 | Chesney et al. ............. | 600/485 |
| 6,017,313 | A * | 1/2000 | Bratteli et al. .............. | 600/485 |
| 6,102,869 | A | 8/2000 | Meier et al. | |
| 6,315,735 | B1 | 11/2001 | Joeken et al. | |
| 2003/0120164 | A1 * | 6/2003 | Nielsen et al. .............. | 600/513 |

FOREIGN PATENT DOCUMENTS

| | | |
|---|---|---|
| DE | 195 33 663 | 3/1997 |
| DE | 197 16 106 | 8/1998 |
| DE | 198 14 371 | 10/1999 |
| DE | 694 21 375 | 7/2000 |
| EP | 0 666 056 | 2/1994 |
| EP | 0 947 941 A2 | 10/1999 |

(Continued)

OTHER PUBLICATIONS

Pergamon *Computers in Biology and Medicine* vol. 32 (2002), pp. 363-377 title: "Simulation of cardiovascular physiology: the diastolic function(s) of the heart" by T. Podnar, F. Runovc and M. Kordas.

(Continued)

*Primary Examiner*—Charles A. Marmor, II
*Assistant Examiner*—Patricia C Mallari
(74) *Attorney, Agent, or Firm*—Collard & Roe, P.C.

(57) ABSTRACT

An apparatus that continuously monitors the arterial pressure measured by a pressure sensor in an artery, which pressure is regarded as the reading Pao that approximately corresponds to the aortal pressure. In principle, the arterial pressure can be measured in the aorta, near the aorta, or in the arterial tree. To provide a second reading, the apparatus, via the input channel, continuously monitors the central venous pressure (CVP), which is regarded as the reading PIT that approximately corresponds to the intrathoracic pressure (ITP). The third reading is provided via the input channel as a reading Z which expresses the thoracic compliance. Via known algorithms of the pulse contour analysis, the apparatus calculates the stroke volume variation, using as the determining pressure the transmural pressure which is calculated according to the formula $$P\text{transmural}=Pao-f(C)*PIT$$

The cardiac volume responsiveness indicator (CVRI) is calculated for mechanical positive respiration according to the formula $$CVRI=k*(SVV/\Delta CVP)$$

or for spontaneous breathing according to the formula $$CVRI=l-m*(\Delta CVP/SVV).$$

58 Claims, 5 Drawing Sheets

FOREIGN PATENT DOCUMENTS

| | | |
|---|---|---|
| JP | 64-86935 | 3/1989 |
| WO | WO 89/00025 | 1/1989 |

OTHER PUBLICATIONS

IEEE Engineering in Medicine & Biology Society 10th Annual International Conference—0063 (1988) "Ventricular Assist by Synchronous, Cardiac Cycle-Specific Increases in Intrathoracic Pressure", by George M. Matuschak and Michael R. Pinsky (2 pages).

*Journal of Applied Physiology*—91:298-308, 2001; "Dynamic effects of positive-pressure ventilation on canine left ventricular pressure-volume relations" by Andre Y. Denault, John Gorcsan, III, and Michael R. Pinsky.

* cited by examiner

*Fig. 1 (Background of the invention)*

APPARATUS FOR DETERMINING CARDIOVASCULAR PARAMETERS

BACKGROUND OF THE INVENTION

1. Field of the Invention

The present invention relates to an apparatus for determining cardiovascular parameters, in particular an apparatus for the continuous determination of the parameters that characterize a patient's left ventricular pumping action, and an apparatus for the continuous determination of the cardiac volume responsiveness indicator.

2. The Prior Art

It is particularly important to monitor continuously cardiovascular parameters in critically ill patients, for example during surgical procedures performed under total anesthesia, or in case of a critical condition. Of special importance are the parameters that characterize the left ventricular pumping action. It is known from the prior art to determine these parameters by means of pulse contour analysis, for which technical solutions such as the commercially available PiCCO system by Pulsion Medical Systems have been known for some time. With these, the parameters to be determined are calculated from the time curve of an arterially measured pressure. In particular, a pulse contour analysis based on a non-linear windkessel model, in which—for example as described in DE 198 14 371 A1—a non-linear function of the pressure measured close to the aorta is used for the so-called compliance (expandability) of the aorta, usually leads to very useful results. However, in patients receiving mechanical respiration, the validity of the information obtained from such an analysis could sometimes be improved.

Furthermore, in the cardiovascular monitoring of intensive-care patients, it is often of crucial importance to recognize whether a critical cardiac filling state of the patient should be treated by supplying volume or with medication. In particular with patients receiving artificial respiration, this is sometimes difficult, since the state of respiration affects the measured variables. This is briefly explained below.

The mammalian thorax can be regarded as a chamber with a variable volume. The chamber is composed of the partial volumes of the heart, the lungs, the extracardiac vessels, and fixed tissue, such as connective tissue and the esophagus. The thoracic volume changes regularly with breathing or mechanical respiration. Under pathophysiological conditions, it may vary due to increased abdominal pressure, and also due to external pressure, for example during diving, etc. Looking at a variable thoracic volume in terms of time, it contains partial volumes which change very rapidly, for example within seconds, in the course of a breathing or respiration cycle, as does the gas volume inside the lungs and the blood volume inside large vessels and inside the heart, and partial volumes which change over longer time periods, such as the functional residual volume of the lungs due to therapeutic intervention, e.g. application of constant positive end-expiratory pressure; an increase in extravasal pulmonary fluid (when a pulmonary oedema is formed), and an increase in pathological partial volumes (as in case of hematothorax, pneumothorax or pleural effusion).

It has been known for a long time that there are interactions between the heart and the lungs during breathing and in particular during mechanical respiration. In the case of spontaneous breathing, the inhaled air enters the lungs due to the negative intrathoracic pressure (ITP) which is produced by the precordial musculature and the diaphragm. However, the venous blood flow into the chest region, often called venous reflux, is facilitated during inhalation as well. During exhalation in spontaneous breathing, the intrathoracic pressure becomes positive again, which causes gas to leave the lungs, since the pressure within in the lungs exceeds atmospheric pressure, while the venous reflux is slowed down. The same happens during mechanical respiration when spontaneous breathing is simulated by means of a respirator in the form of an iron lung.

During the most common form of mechanical respiration, i.e. positive-pressure respiration, inhaling is accomplished by producing a positive pressure in the airways of the breathing apparatus outside the lungs. Respiratory gas enters the lungs because the gas pressure inside the lungs is lower. Gas enters the lungs until the pressure in the external airways and the gas pressure in the lungs and internal airways reach an equilibrium. During this inhalation process, the lungs are enlarged, which increases the intrathoracic pressure, and the large blood vessels and the heart itself are compressed. Physiologically, this means that venous reflux is reduced. Exhalation occurs due to the retractive force of the thoracic wall and the lungs themselves and, to a lesser degree, due to the weight of the thoracic wall itself, whereby the intrathoracic pressure (ITP) drops again while the venous reflux increases.

Figure 1:
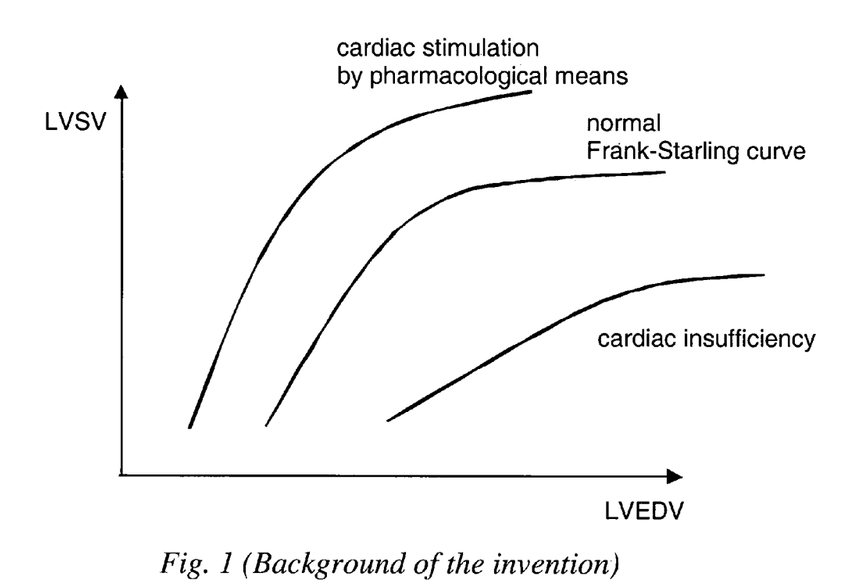
FIG. 1 shows as a background to the invention, a Frank Starling curve and its change due to cardiac stimulation by pharmacological means, and due to cardiac insufficiency.

The above described changes in venous reflux during spontaneous breathing as well as during mechanical positive respiration have a direct effect on the cardiac filling and— via the so-called Frank Starling mechanism—on the ventricular output, i.e. the stroke volume. In simplified terms, the Starling mechanism describes a relationship between the diastolic cardiac filling volume and the cardiac stroke volume. The more the heart is filled in the diastolic phase, the greater is the output of cardiac stroke volume. This relationship is predominantly linear in a normal heart and becomes flatter when a normally contracting heart is overfilled in the diastolic phase. This is shown in FIG. 1, where the left ventricular stroke volume (LVSV) is plotted schematically against the left ventricular end-diastolic volume (LVEDV) which essentially corresponds to the filling status in the diastolic phase. The middle curve shows the normal pattern. When positively inotropic substances such as adrenalin are administered, i.e. when the cardiac contraction force is increased, the Starling curve shifts to the left, whereas conditions connected with an acutely or chronically changed cardiac contraction force reduce the rise and cause a shift of the curve to the right. The response to a volume increase can be just as varied while the measured end-diastolic volume remains the same.

In the case of spontaneous breathing or mechanical positive respiration, the effects on cardiac filling, especially on the filling of the right ventricle, cause a variable stroke volume of the right ventricle which in turn affects the filling and the output of the left ventricle after perfusion of the lungs. Finally, these changes in cardiac filling can be detected by measuring the periodic fluctuations of the aortic or arterial pressure curve which directly reflect the changes in the left ventricular volume output.

EP 0 666 056 B1 discloses an apparatus for evaluating the necessity of providing instantaneous volume or evaluating how a patient under artificial respiration responds to the intravenous administration of volume substitutes, wherein the systolic pressure variation serves as an indicator of how receptive the patient is to volume. However, with this apparatus, it is necessary to measure the tidal volume or the respiration pressure of the respirator, and to compare it to the hemodynamic pressure before any conclusions can be drawn. It is not possible to take all interactions between the state of respiration and the measured cardiovascular values into full consideration. Furthermore, the prior art apparatus does not provide any information as to what happens when the patient returns to spontaneous breathing.

SUMMARY OF THE INVENTION

Against the backdrop of the above described problems, the object of the present invention is to create an apparatus for determining parameters that characterize a patient's left ventricular pumping action without lessening the validity of measuring results through the effect of respiration and changing respiratory states. It is also an object of the present invention to create an apparatus for determining a parameter that allows a reliable evaluation of the cardiac volume responsiveness, i.e. of the readiness for a supply of volume even with variable respiration states.

According to one aspect of the invention, this object is achieved by an apparatus for the continuous determination of a parameter characterizing a patient's left ventricular pumping action comprising:

a first input channel for the continuous recording of a variable physiological first reading directly dependent on the left ventricular pumping action, and an evaluation unit for calculating said parameter characterizing the left ventricular pumping action, wherein the apparatus also comprises a second input channel for the continuous recording of a variable physiological second reading which at least approximately indicates the patient's intrathoracic pressure (ITP) or is dependent on same, and wherein the evaluation unit is programmed for calculating the parameter characterizing the patient's left ventricular pumping action from said first reading, using a corrective function based on said second reading.

According to another aspect of the invention, this object is achieved by an apparatus for the continuous determination of the cardiac volume responsiveness indicator comprising a first input channel for the continuous recording of a variable physiological first reading directly dependent on the patient's left ventricular pumping action, a second input channel for the continuous recording of a variable physiological second reading at least approximately representing the patient's intrathoracic pressure (ITP), a third input channel for the continuous recording of a third reading which depends directly on the patient's state of respiration, and an evaluation unit for calculating said cardiac volume responsiveness indicator. The evaluation unit is programmed to use said second and third readings to select a function that can be used for the patient's current state of respiration and based on this function, to calculate sid volume responsiveness indicator from said first and second readings.

The periodic fluctuations of the right or left ventricular stroke volume caused by interaction between heart and lungs, or the measured periodic fluctuations of another physiological signal, which correspond to or reflect the periodic fluctuations of the right or left ventricular output of the stroke volume, such as pressure curves measured in the Arteria pulmonalis, the aorta or the arterial tree, or periodic fluctuations of the signal of plethysmographic pulse oximetry, are used to diagnose the heart's response to changing cardiac filling conditions, i.e. to diagnose the heart's pre-load volume. As described above, these periodic fluctuations, which depend on breathing or artificial respiration, indicate that the heart responds to changes in the cardiac pre-load volume. These fluctuations are caused by the effect of the changing ITP on the volume of the intrathoracic low pressure capacitance system (ITLPCS) consisting of the Venae cava superior and inferior, the right atrium, the right ventricle in the diastolic phase, the pulmonary vascular system, and the left atrium. The ITLPCS is characterized by a low mean intravascular pressure and a relatively large intravascular volume. In the ITLPCS, the connection between volume and pressure is non-linear, which means that the pressure is very low at a low volume while the mean intravascular pressure increases progressively as the volume increases. In other words, with hypovolemia, changes in ITLPCS volume have little effect on pressure, while with hypervolemia, any change in ITLPCS volume has a great effect on the mean ITLPCS pressure. Any change in the intrathoracic pressure, which is the pressure surrounding the ITLPCS, is transferred directly to the intravascular pressure inside the ITLPCS due to the very high compliance of the vascular structures contained in the ITLPCS. The transmural pressure of the ITLPCS can be estimated as the difference between intravascular pressure and the intrathoracic pressure. The effective transmural pressure in the ITLPCS determines the actual vascular dilation and thus the volume within the ITLPCS.

Hence, a constant breath, such as a mechanical breath of constant depth, causes the same change in ITP, but—depending on the volume state of the ITLPCS—it affects the cardiac pre-load and thus the stroke volume to a varying degree. The main portion of the ITLPCS consists of the Venae cavae superior and inferior, the right atrium and the right ventricle in the diastolic phase while it is under the lowest mean intravascular pressure. Therefore, the effects on the ITP caused by breathing or artificial respiration greatly influence the right ventricular end-diastolic volume (RVEDV) and subsequently the right ventricular stroke volume (RVSV), but they have much less direct influence on the left ventricular end-diastolic volume (LVEDV) and the left ventricular stroke volume (LVSV). Over time, however, after passage through the lungs, these effects on the right ventricular stroke volume can also be detected in the form of changes in the left ventricular end-diastolic volume and the left-ventricular stroke volume.

For that reason, the same amount of breathing will have a much greater effect on the development of the left ventricular stroke volume with hypovolemia than with hypervolemia, provided that the left ventricle responds to changes in the pre-load. With the help of the apparatus according to the invention, the totality of these relationships can be used clinically for examining the volume responsiveness of the left ventricle. As a clinical consequence, a patient whose left heart responds to volume, which means that his heart works in a steeper section of its current Starling curve, would be supplied with volume to optimize his cardiac output (CO). On the other hand, the supply of volume would be avoided in a patient whose left heart does not respond to volume, since his heart works in the flat section of its current Starling curve. Instead, one would try to optimize his cardiac output by administering positively inotropic substances to shift his function curve into a steeper form (left shift, see FIG. 1).

This information is very valuable for anesthetists or intensive-care specialists. It can be obtained easily and fully automatically with a monitoring system designed along the principles of the apparatus according to the invention. Such a system continuously supplies the stroke volume or any variable reflecting the stroke volume and provides the information as to which type and phase of breathing or mechanical respiration is predominant or being applied, and how the intrathoracic pressure is affected by this kind of breathing or respiration measure.

This approach has the advantage that the heart/lung interaction used for examining the cardiac volume responsiveness can be standardized for spontaneous breathing as well as for mechanical respiration by measuring the change in intrathoracic pressure it causes, while the individual breath volume does not necessarily have to be standardized and does not have to follow a certain pattern, but may be of any magnitude.

On the other hand, there would not be much sense in trying to standardize values which describe breathing itself, since the degree to which the ITLPCS is influenced depends on the compliance of the respiratory tract itself, on the compliance of the thoracic wall and on the presence of a space-occupying process with a low time constant such as a pulmonary oedema, pneumothorax, hematothorax or pleural effusion. The tidal volume (=breath volume) and all above named factors contribute to changes in ITP, which directly affects the ITPLCS. For that reason, effects caused by breathing/respiration are best standardized by taking into account the changes in ITP which accompany them. Phase-related changes in ITP can be derived directly from changes in the continuously monitored central venous pressure (CVP) if changes in the thoracic dimensions are recorded at the same time or (applicable only in the case of mechanical positive-pressure respiration) if the timing and the form of mechanical respiration can be derived from the pressure of the respiratory system measured close to the patient, thus avoiding any time lag.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 2:
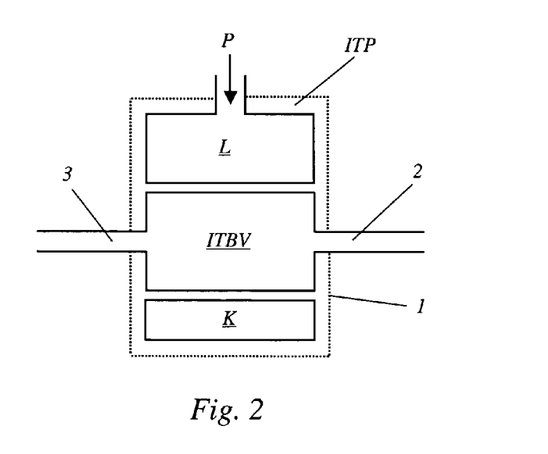
FIG. 2 shows the basic interaction between different volumes and the intrathoracic pressure.

FIG. 2 shows a schematic view of the volumes affected by or affecting the intrathoracic pressure (ITP) and other characteristic pressures that are of significance in connection with the invention. Inside thoracic wall 1, the ITP acts upon the intrathoracic blood volume (ITBV) which is composed of the above named intrathoracic low-pressure capacitance system (ITLPCS) and the left ventricular end-diastolic volume (LVEDV). Other volumes inside thoracic wall 1 are the gas-filled lung volume L and, if applicable, additional volumes K, such as extravascular lung fluid, pleural effusion, hematothorax, etc., which must be regarded as constant during a measuring period. Aortal pressure AP prevails in the aorta 2 while central venous pressure CVP prevails in the central vein 3. In the case of artificial respiration, the airways are subject to external pressure P.

Figure 3:
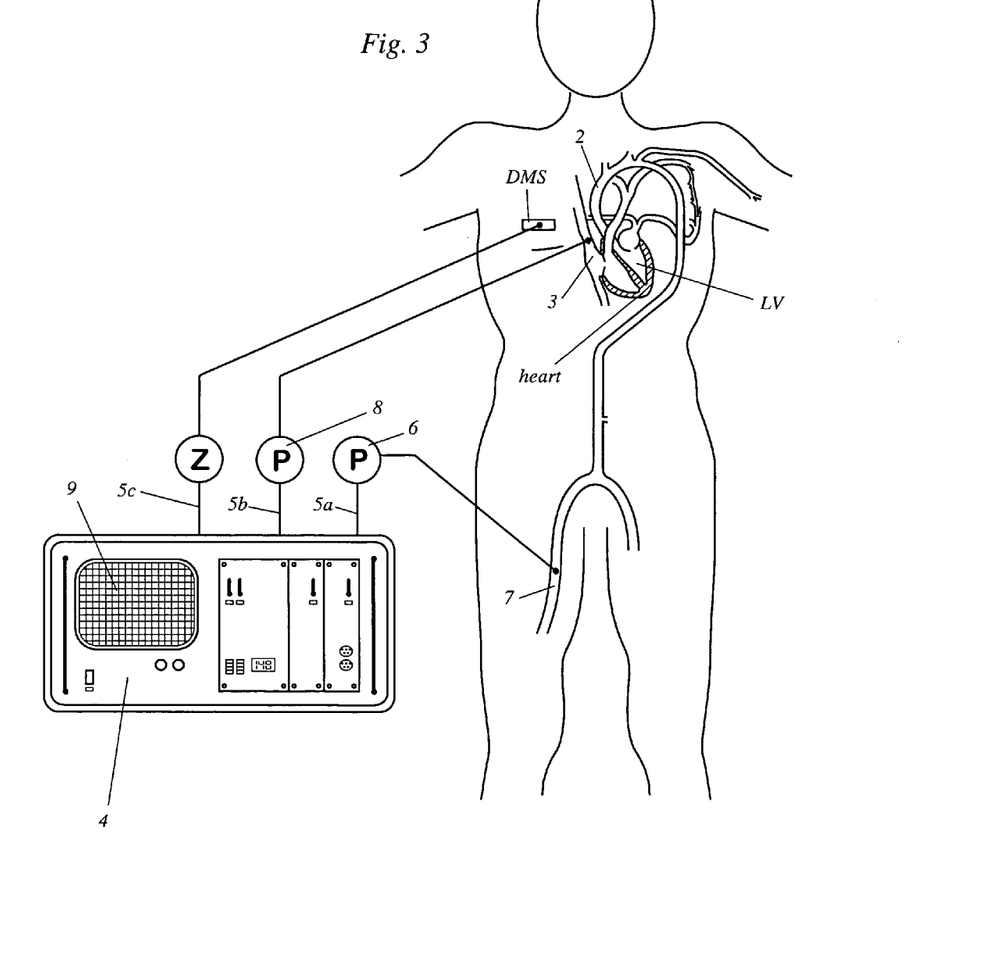
FIG. 3 shows an apparatus according to the invention being applied to a patient.

The apparatus 4 shown in FIG. 3, via input channel 5a, continuously monitors the arterial pressure measured by the pressure sensor 6 in an artery 7. Said arterial pressure must be regarded as a reading Pao which at least approximately corresponds to the aortal pressure. In principle, the arterial pressure can be measured in the aorta 2, in its vicinity, or in the arterial tree. A second reading, the central venous pressure (CVP), which is measured by pressure sensor 8 in central vein 2, is provided continuously by apparatus 4 via input channel 5b. The CVP is regarded as a pressure $P_{IT}$ which approximately corresponds to the ITP. The third reading, which is given via input channel 5c, is a parameter Z that reflects the thoracic compliance. Measuring may be performed, for example, with a strain gauge (DMS), but it is also possible to measure another reading which directly or indirectly represents thoracic compliance in absolute or relative terms.

Figure 4A:
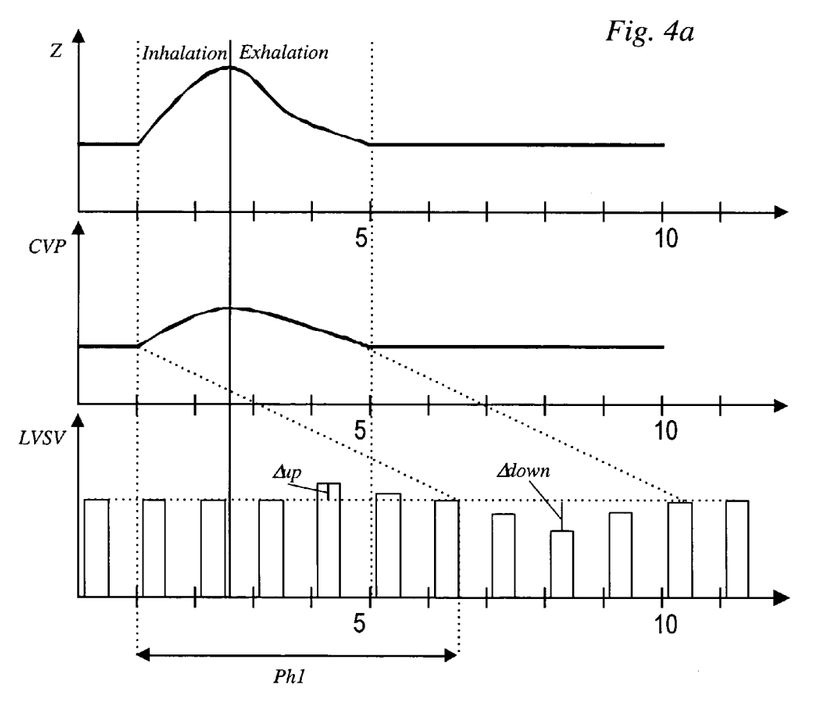
FIG. 4a is a schematic representation of the temporal variability (change vs. time) of the readings which determine the calculation of the volume responsiveness indicator in case of positive pressure respiration.
Figure 4B:
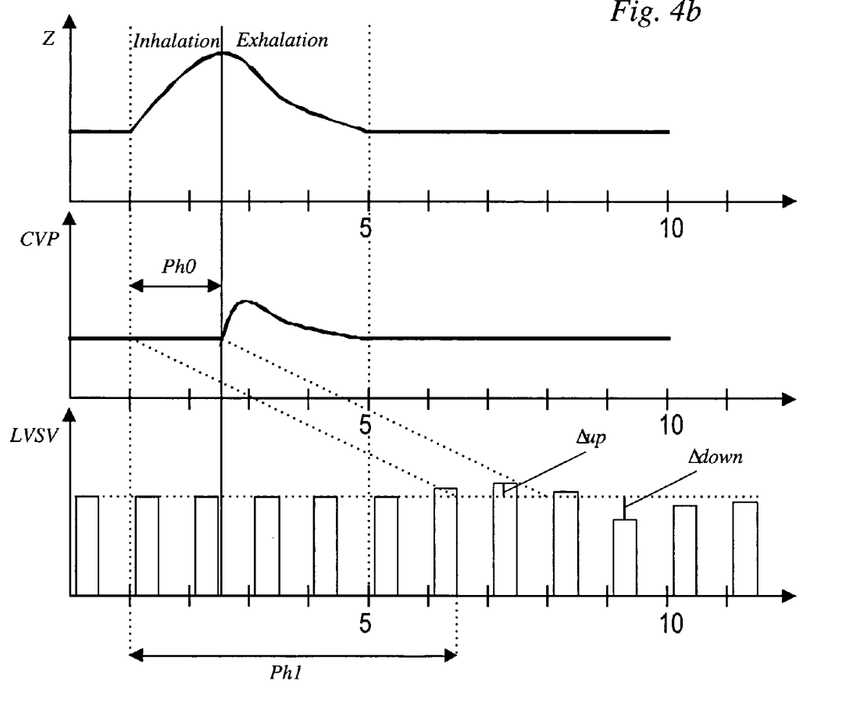
FIG. 4b is a schematic representation of the temporal variability of the readings which determine the calculation of the volume responsiveness indicator in case of spontaneous breathing.

Typically obtained timing sequences for thoracic dimension Z (upper diagrams) and the central venous pressure (CVP) are shown in FIG. 4a for mechanical positive pressure respiration and in FIG. 4b for spontaneous breathing. The abscissa is the time axis with cardiac pulse cycles as the axis unit.

By means of conventional algorithms of pulse contour analysis, the appropriately programmed apparatus 4 calculates the stroke volume (LVSV) (lower diagrams in FIGS. 4a and 4b) of the left ventricle (LV), the stroke volume variation SVV, and if applicable other desired cardiovascular readings. The transmural pressure is calculated as the relevant pressure, according to the following formula:

$$P_{transmural} = Pao - f(C) * P_{IT}$$

The function f(C) is a function of compliance (C) of the arterial system or primarily the aorta 2, where compliance is preferably determined according to a non-linear windkessel model, and the function f(C) can, for example, take the form of $$f(C) = 1 - \exp(-a*C)$$

with (a) as the adaptation parameter, but which in any case increases monotonically as the compliance increases and may assume values between 0 and 1.

A phase shift Ph1 must be taken into consideration due to the transpulmonary and left ventricular path. As an alternative to the stroke volume variation SVV, only the upward (Δup) or downward (Δdown) deviations of the stroke volume could be taken into consideration. Δup and Δdown may also be required for calculating other desired cardiovascular parameters.

The phase shift Ph0 between the beginning of the rise of the thoracic dimension curve Z, i.e. beginning thoracic compliance, and the beginning of the rise of the curve of the central venous pressure CVP indicates whether mechanical respiration or spontaneous breathing is taking place. Such a phase shift Ph0 is noticeable only with spontaneous breathing (FIG. 4b) but not with mechanical positive pressure respiration (FIG. 4a). However, the less distinct phase shift of the local maximums of the curves of thoracic dimension Z and the central venous pressure can also be used as an alternative criterion.

Figure 5A:
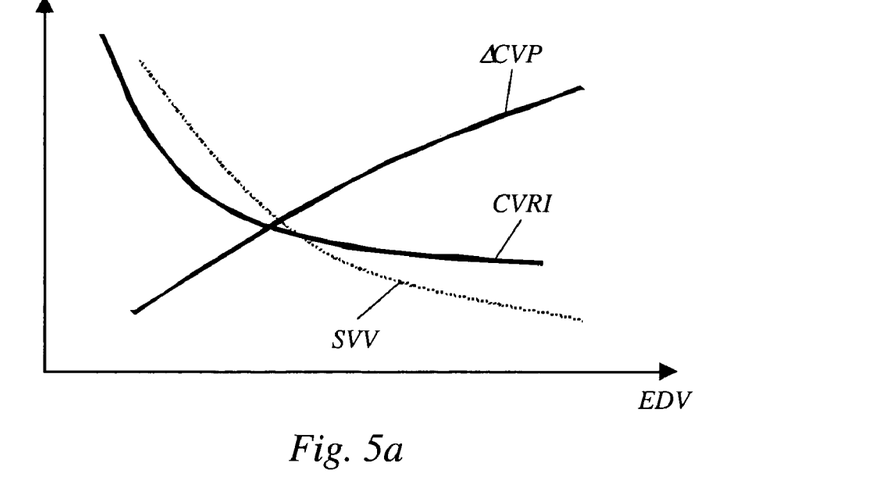
FIG. 5a shows a schematic view of the course of the volume responsiveness indicator depending on the end-diastolic volume with positive pressure respiration.
Figure 5B:
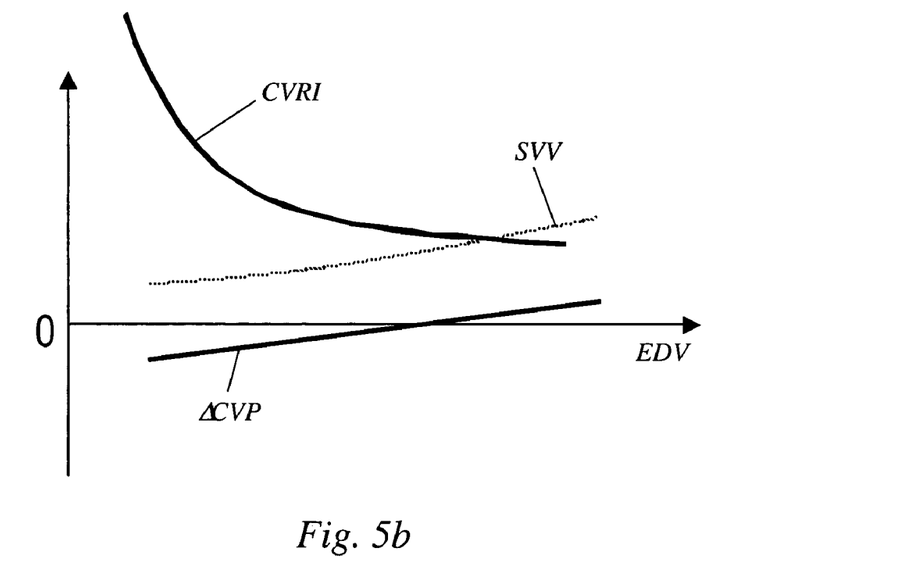
FIG. 5b shows a schematic view of the course of the volume responsiveness indicator depending on the end-diastolic volume with spontaneous breathing.

By means of the above explained criterion, it is decided whether the cardiac volume responsiveness indicator (CVRI) should be calculated according to the formula $$CVRI=k*(SVV/\Delta CVP)$$

for mechanical positive-pressure respiration, or according to the formula $$CVRI=l-m*(\Delta CVP/SVV)$$

for spontaneous breathing, where $\Delta CVP$ is the variation of the central venous pressure during a breathing cycle. The curves obtained as a function of the end-diastolic volume EDV are shown in FIG. 5a for positive pressure respiration and in FIG. 5b for spontaneous breathing.

The k, l and m values are adaptation parameters. As a rule, these would be estimated or experimentally determined constants, but suitable adaptation functions can be used as well, for example with the goal being that both functions provide the same value in their application range when the EDV for the patient's cardiac volume responsiveness indicator has the same value.

Monitor 9 provides the calculated CVRI together with the calculated cardiac output (CO), and—if the patient's filling status is unsatisfactory—this CVRI can help the attending physician to decide whether volume must be supplied or medication is preferable.

Accordingly, while only a few embodiments of the present invention have been shown and described, it is obvious that many changes and modifications may be made thereunto without departing from the spirit and scope of the invention.

What is claimed is:

1. An apparatus for the continuous determination of a parameter characterizing a patient's left ventricular pumping action, comprising
    a first input channel for continuous recording of a variable physiological first reading directly dependent on the left ventricular pumping action, and
    an evaluation unit for calculating said parameter characterizing the left ventricular pumping action,
    wherein said apparatus also comprises a second input channel for continuous recording of a variable physiological second reading which at least approximately indicates the patient's intrathoracic pressure (ITP) or is dependent on same,
    wherein said evaluation unit is programmed for calculating the parameter characterizing the patient's left ventricular pumping action from said first reading, using a corrective function based on said second reading,
    wherein said corrective function takes into account periodic fluctuations of said second reading.

2. The apparatus according to claim 1, wherein said first input channel is configured for reading a pressure transducer signal, wherein said first reading at least approximately corresponds to the patient's aortic pressure, and wherein programming of the evaluation unit allows the calculation of said parameter characterizing the patient's left ventricular pumping action by means of a pulse contour analysis.

3. The apparatus according to claim 2, wherein said first reading which at least approximately corresponds to the aortic pressure is an arterial pressure.

4. The apparatus according to claim 3, wherein said arterial pressure is a pressure measured close to the aorta.

5. The apparatus according to claim 2, wherein said pulse contour analysis is based on a non-linear windkessel model.

6. The apparatus according to claim 2, wherein the corrective function has the form of $$P_{transmural}=Pao-f(C)*P_{IT}$$

wherein
    Pao is said first reading which at least approximately corresponds to the aortic pressure,
    $P_{IT}$ is said second reading which at least approximately expresses the intrathoracic pressure (ITP), and
    f(C) is a function which depends on the compliance (C) of the arterial system or the aorta and which increases monotonically as the compliance increases and may assume values between 0 and 1, and wherein the transmural pressure ($P_{transmural}$) is the determining pressure in the pulse contour analysis.

7. The apparatus according to claim 6, wherein said function f(C) has the formula $$f(C)=1-\exp(-a*C)$$

wherein exp(-a*C) is an exponential function with argument -a*C, wherein (C) is compliance of the arterial system or the aorta, and (a) is an estimated or experimentally determined constant.

8. The apparatus according to claim 7, wherein a dependence of the compliance (C) on the transmural pressure ($P_{transmural}$) is assumed and that both of these values are calculated by means of iteration.

9. The apparatus according to claim 1, wherein said second input channel is configured for reading a pressure transducer signal, and wherein said second reading at least approximately corresponds to the patient's central venous pressure (CVP).

10. The apparatus according to claim 1, wherein said parameter that characterizes the patient's left ventricular pumping action is one of a group of cardiac output, stroke volume and a parameter directly calculated from those.

11. An apparatus for the continuous determination of the cardiac volume responsiveness indicator, comprising:
    a first input channel for the continuous recording of a variable physiological first reading directly dependent on a patient's left ventricular pumping action,
    a second input channel for continuous recording of a variable physiological second reading at least approximately representing the patient's intrathoracic pressure (ITP),
    a third input channel for continuous recording of a third reading which depends directly on the patient's state of respiration, and
    an evaluation unit for calculating said cardiac volume responsiveness indicator,
    wherein the evaluation unit is programmed to use said second and third readings to select a function that can be used for the patient's current state of respiration and based on this function, to calculate said volume responsiveness indicator from said first and second readings.

12. The apparatus according to claim 11, wherein said first reading is a size of the left ventricle which is determined by means selected from the group consisting of X ray densitometry, positron emission tomography, transesophageal echo cardiography, transthoracic echo cardiography and other two- or three-dimensional imaging techniques.

13. The apparatus according to claim 11, wherein said first reading which depends on the patient's left ventricular pumping function is a reading determined by a measurement selected from the group consisting of plethysmography, measuring the electric impedance, measuring the electric conductivity, ultrasound, measuring the pressure in the Arteria pulmonalis, and direct flow measurement.

14. The apparatus according to claim 11, wherein said first input channel (5a) is configured for reading a pressure transducer signal, and wherein said first reading at least approximately corresponds to the patient's aortic pressure.

15. The apparatus according to claim 11, wherein said evaluation unit is programmed to calculate from the temporal variability of said first reading at least one of a value selected from the group consisting of stroke volume variation (SVV), systolic pressure variation (SPV), pulse pressure variation (PPV) and a similar value.

16. The apparatus according to claim 14, wherein said evaluation unit is programmed to calculate at least one of a value selected from the group consisting of stroke volume variation (SVV), systolic pressure variation (SPV), pulse pressure variation (PPV) and a similar value, from the first reading by means of pulse contour analysis, using a corrective function formed with the second reading.

17. The apparatus according to claim 16, wherein said corrective function has the formula:

$$P_{transmural} = Pao - f(C) * P_{IT}$$

wherein Pao is said first reading which at least approximately corresponds to the aortic pressure, $P_{IT}$ is said second reading which at least approximately expresses the intrathoracic pressure (ITP), and f(C) is a function which depends on compliance (C) of the arterial system or the aorta and which increases monotonically as the compliance increases and may assume values between 0 and 1, and wherein transmural pressure ($P_{transmural}$) is a determining pressure in the pulse contour analysis.

18. The apparatus according to claim 17, wherein said function f(C) has the formula $$f(C) = 1 - \exp(-a*C)$$

wherein exp(-a*C) is an exponential function with argument -a*C, wherein (C) is compliance of the arterial system or of the aorta (2), and (a) is an estimated or experimentally determined constant.

19. The apparatus according to claim 18, wherein a dependence of the compliance (C) on transmural pressure ($P_{transmural}$) is assumed and that both of these values are calculated by means of iteration.

20. The apparatus according to claim 11, wherein selection of the function to be applied to the patient's current respiration status consists of a choice between a first function valid for the artificial respiration of the patient and a second function valid for the patient's spontaneous breathing.

21. The apparatus according to claim 20, wherein said first function valid for the artificial respiration of the patient has the formula $$CVRI = k * (XXV / \Delta P_{IT})$$

and that said second function valid for the patient's spontaneous breathing has the formula $$CVRI = l - m * (\Delta P_{IT} / XXV)$$

wherein CVRI is the cardiac volume responsiveness indicator, XXV is one of the group of stroke volume variation (SVV), systolic pressure variation (SVP), pulse pressure variation (PPV) and a similar value describing the left ventricular pumping function, $\Delta P_{IT}$, is the variation of said second reading which at least approximately expresses the intrathoracic pressure (ITP) during a breathing cycle, and wherein k, l and m are adaptation parameters.

22. The apparatus according to claim 21, wherein said adaptation parameters k, l and m are adaptation functions.

23. The apparatus according to claim 21, wherein said adaptation parameters k, l and m are estimated or experimentally calculated constants.

24. The apparatus according to claim 23, wherein said adaptation parameters k, l and m are selected such that both functions result in a same value in their application range when an end-diastolic volume for the patient's cardiac volume responsiveness indicator (CVRI) remains the same.

25. The apparatus according to claim 20, wherein the programming of the evaluation unit allows for determination of an onset of the patient's inhalation based on temporal variability of said third reading; and the determination whether said first function valid for the artificial respiration of the patient or said second function valid for the patient's spontaneous breathing should be used, depending on a phase shift between the onset of inhalation and the beginning of the rise of said second reading which at least approximately expresses the intrathoracic pressure (ITP), such that artificial respiration has to be assumed for a phase shift lying below a threshold value between the onset of inhalation and the beginning of the rise of said second reading, and spontaneous breathing has to be assumed for a phase shift lying above a threshold value between the onset of inhalation and the beginning of the rise of said second reading.

26. The apparatus according to claim 11, wherein said third reading at least approximately corresponds to the patient's thoracic compliance.

27. The apparatus according to claim 26, wherein said third input channel is configured for reading one of the group of a strain gauge (DMS) or a sensor measuring the impedance.

28. The apparatus according to claim 11, wherein said third reading at least approximately corresponds to one of the group of the respiration pressure and the volume flow of the patient's tidal air.

29. The apparatus according to claim 11, wherein said second input channel is configured for reading a pressure transducer signal, and wherein said second reading at least approximately corresponds to the patient's central venous pressure.

30. A method of continuous determination of a parameter characterizing a patient's left ventricular pumping action, comprising the steps of:
  recording a variable physiological first reading directly dependent on the left ventricular pumping action;
  continuously recording a variable physiological second reading which at least approximately indicates the patient's intrathoracic pressure (ITP) or is dependent on same; and
  calculating said parameter characterizing the left ventricular pumping action from said first reading, using a corrective function based on said second reading;
  wherein said corrective function takes into account periodic fluctuations of said second reading.

31. The method of claim 30, wherein said first reading is taken from a pressure transducer signal which at least approximately corresponds to the patient's aortic pressure, and wherein said parameter characterizing the patient's left ventricular pumping action is calculated by means of a pulse contour analysis.

32. The method according to claim 31, wherein said first reading which at least approximately corresponds to the aortic pressure is an arterial pressure.

33. The method according to claim 32, wherein said arterial pressure is a pressure measured close to the aorta.

34. The method according to claim 31, wherein said pulse contour analysis is based on a non-linear windkessel model.

35. The method according to claim 31, wherein the corrective function has the form of $$P_{transmural} = Pao - f(C) * P_{IT}$$

wherein

Pao is said first reading which at least approximately corresponds to the aortic pressure, $P_{IT}$ is said second reading which at least approximately expresses the intrathoracic pressure (ITP), and f(C) is a function which depends on compliance (C) of the arterial system or the aorta and which increases monotonically as the compliance increases and may assume values between 0 and 1, and wherein transmural pressure ($P_{transmural}$) is the determining, pressure in the pulse contour analysis.

36. The method according to claim 35, wherein said function f(C) has the formula $$f(C) = 1 - \exp(-a*C)$$

wherein exp(a*C) is the exponential function with the argument −a*C, wherein (C) is the compliance of the arterial system or the aorta, and (a) is an estimated or experimentally determined constant.

37. The method according to claim 36, wherein a dependence of the compliance (C) on the transmural pressure ($P_{transmural}$) is assumed, and both of these values are calculated by means of iteration.

38. The method according to claim 30, wherein said second reading is taken from a pressure transducer signal, and wherein said second reading at least approximately corresponds to the patient's central venous pressure (CVP).

39. The method according to claim 30, wherein said parameter that characterizes the patient's left ventricular pumping action is selected from the group consisting of cardiac output, stroke volume and a parameter directly calculated from those.

40. A method of continuous determination of the cardiac volume responsiveness indicator, comprising the steps of
recording a variable physiological first reading directly dependent on the patient's left ventricular pumping action,
recording a variable physiological second reading at least approximately representing the patient's intrathoracic pressure (ITP),
recording a third reading which depends directly on the patient's state of respiration,
using said second and third readings to select a function that can be used for the patient's current state of respiration, and, based on this function,
calculating said cardiac volume responsiveness indicator from said first and second readings.

41. The method according to claim 40, wherein said first reading is the size of the left ventricle which is determined by means of a method selected from the group consisting of X ray densitometry, positron emission tomography, transesophageal echo cardiography, transthoracic echo cardiography and other two- or three-dimensional imaging techniques.

42. The method according to claim 40, wherein said first reading which depends on the patient's left ventricular pumping function is a reading determined by a measurement selected from the group consisting of plethysmography, measuring electric impedance, measuring electric conductivity, ultrasound, measuring pressure in Arteria pulmonalis, and direct flow measurement.

43. The method according to claim 40, wherein said first reading is taken from a pressure transducer signal, and wherein said first reading at least approximately corresponds to the patient's aortic pressure.

44. The method according to claim 40, wherein from the temporal variability of said first reading at least one of the group of stroke volume variation (SVV), systolic pressure variation (SPV), pulse pressure variation (PPV) and a similar value is calculated.

45. The method according to claim 44, wherein said evaluation one of the group of stroke volume variation (SVV), systolic pressure variation (SPV), pulse pressure variation (PPV) and a similar value, is calculated from said first reading by means of pulse contour analysis, using a corrective function formed with the second reading.

46. The method according to claim 45, wherein said corrective function has the formula $$P_{transmural} = Pao - f(C) * P_{IT}$$

wherein

Pao is said first reading which at least approximately corresponds to the aortic pressure, $P_{IT}$ is said second reading which at least approximately expresses the intrathoracic pressure (ITP), and f(C) is a function which depends on compliance (C) of the arterial system or the aorta and which increases monotonically as the compliance increases and may assume values between 0 and 1, and wherein the transmural pressure ($P_{transmural}$) is the determining pressure in the pulse contour analysis.

47. The method according to claim 46, wherein said function f(C) has the formula $$f(C) = 1 - \exp(-a*C)$$

wherein exp(−a*C) is the exponential function with argument −a*C, wherein (C) is compliance of the arterial system or of the aorta (2), and (a) is an estimated or experimentally determined constant.

48. The method according to claim 47, wherein a dependence of the compliance (C) on the transmural pressure ($P_{transmural}$) is assumed and that both of these values are calculated by means of iteration.

49. The method according to claim 40, wherein selection of the function to be applied to the patient's current respiration status consists of a choice between a first function valid for the artificial respiration of the patient and a second function valid for the patient's spontaneous breathing.

50. The method according to claim 49, wherein said first function valid for the artificial respiration of the patient has the formula $$CVRI = k * (XXV / \Delta P_{IT})$$

and that said second function valid for the patient's spontaneous breathing has the formula $$CVRI = l - m * (\Delta P_{IT} / XXV)$$

wherein CVRI is the cardiac volume responsiveness indicator, XXV is selected from the group consisting of stroke volume variation (SVV), systolic pressure variation (SVP), pulse pressure variation (PPV) and a similar value describing the left ventricular pumping function, $\Delta P_{IT}$ is the variation of said second reading which at least approximately expresses the intrathoracic pressure (ITP) during a breathing cycle, and wherein k, l and m are adaptation parameters.

51. The method according to claim 50, wherein said adaptation parameters k, l and m are adaptation functions.

52. The method according to claim 50, wherein said adaptation parameters k, l and m are estimated or experimentally calculated constants.

53. The method according to claim 52, wherein said adaptation parameters k, l and m are selected such that both functions result in a same value in their application range when an end-diastolic volume for the patient's cardiac volume responsiveness indicator (CVRI) remains the same.

54. The method according to claim 49, wherein the onset of the patient's inhalation is determined based on the temporal variability of said third reading; and it is determined whether said first function valid for the artificial respiration of the patient or said second function valid for the patient's spontaneous breathing should be used, depending on the phase shift between the onset of inhalation and the beginning of the rise of said second reading which at least approximately expresses the intrathoracic pressure (ITP), such that artificial respiration has to be assumed for a phase shift lying below a threshold value between the onset of inhalation and the beginning of the rise of said second reading, and spontaneous breathing has to be assumed for a phase shift lying above a threshold value between the onset of inhalation and the beginning of the rise of said second reading.

55. The method according to claim 40, wherein said third reading at least approximately corresponds to the patient's thoracic compliance.

56. The method according to claim 55, wherein said third reading is taken from a signal of a strain gauge (DMS) or a sensor measuring the impedance.

57. The method according to claim 56, wherein said third reading at least approximately corresponds to one of the respiration pressure and the volume flow of the patient's tidal air.

58. The method according to claim 40, wherein said second reading is taken from a pressure transducer signal, and wherein said second reading at least approximately corresponds to the patient's central venous pressure.

* * * * *